(12) United States Patent
Liu et al.

(10) Patent No.: US 10,773,098 B2
(45) Date of Patent: Sep. 15, 2020

(54) THERAPY FOR GLIOBLASTOMA MULTIFORME

(71) Applicant: National Yang-Ming University, Taipei (TW)

(72) Inventors: Tse-Ying Liu, Taipei (TW); Ming-Hong Chen, Taipei (TW)

(73) Assignee: National Yang-Ming University, Taipei (TW)

( * ) Notice: Subject to any disclaimer, the term of this patent is extended or adjusted under 35 U.S.C. 154(b) by 264 days.

(21) Appl. No.: 15/878,279

(22) Filed: Jan. 23, 2018

(65) Prior Publication Data

US 2018/0207447 A1     Jul. 26, 2018

Related U.S. Application Data

(60) Provisional application No. 62/449,811, filed on Jan. 24, 2017.

(51) Int. Cl.

| | |
|---|---|
| *A61N 5/10* | (2006.01) |
| *A61K 31/197* | (2006.01) |
| *A61N 7/00* | (2006.01) |
| *A61P 35/00* | (2006.01) |
| *A61K 47/02* | (2006.01) |
| *A61K 9/00* | (2006.01) |
| *A61K 9/51* | (2006.01) |
| *A61K 47/36* | (2006.01) |

(52) U.S. Cl.
CPC .............. *A61N 5/10* (2013.01); *A61K 9/0009* (2013.01); *A61K 9/5161* (2013.01); *A61K 31/197* (2013.01); *A61K 47/02* (2013.01); *A61K 47/36* (2013.01); *A61N 7/00* (2013.01); *A61P 35/00* (2018.01); *A61N 2005/1098* (2013.01)

(58) Field of Classification Search
CPC ...... A61N 5/10–1084; A61N 7/00–022; A61N 2005/1098
See application file for complete search history.

(56) References Cited

U.S. PATENT DOCUMENTS

| 5,817,048 A * | 10/1998 | Lawandy | A61K 41/0033 604/20 |
|---|---|---|---|
| 2003/0082101 A1* | 5/2003 | Taylor | A61K 41/0028 424/1.11 |
| 2004/0181114 A1* | 9/2004 | Hainfeld | A61K 41/0038 600/1 |
| 2004/0234497 A1* | 11/2004 | Luo | A61K 31/704 424/85.1 |
| 2005/0112131 A1* | 5/2005 | Pogue | A61K 41/0057 424/178.1 |
| 2017/0056351 A1* | 3/2017 | Nishizawa | A61K 33/26 |

FOREIGN PATENT DOCUMENTS

WO    WO-2016196783 A1 *  12/2016  ............ A61N 5/00

* cited by examiner

*Primary Examiner* — Catherine B Kuhlman
(74) *Attorney, Agent, or Firm* — Muncy, Geissler, Olds & Lowe, P.C.

(57) ABSTRACT

The invention provides a therapy method for glioblastoma multiforme (GBM). The therapy method uses a low-dose radiation to realize GBM tumor cell-targeted radiotherapy via sequentially administration of radiation enhancer-incorporated nanocarriers, 5-aminolevulinic acid, therapeutic ultrasound and therapeutic radiation.

5 Claims, 12 Drawing Sheets
(1 of 12 Drawing Sheet(s) Filed in Color)

THERAPY FOR GLIOBLASTOMA MULTIFORME

CROSS-REFERENCE TO RELATED APPLICATION

This is a non-provisional application of U.S. Provisional Application No. 62/449,811, filed on Jan. 24, 2017.

BACKGROUND OF THE INVENTION

1. Field of the Invention

The present invention relates to a therapy method for glioblastoma multiforme (GBM), and more in particular, to a therapy method for GBM combining with a sonodynamic therapy and a radiotherapy with low dose radiation.

2. Description of the Prior Art

Radiotherapy is one of the main therapeutic approaches utilized to treat cancer. However, radiotherapy often causes serious side effects. Although some tumor tissue-focused radiation therapies, such as image-guided radiotherapy and intensity modulation radiotherapy, appear to lower radiation-induced lesion formation, it is difficult to achieve tumor cell-targeted radiotherapy (i.e., precisely focus the radiation energy to tumor cells) only using these techniques. This issue has largely been addressed by the development of boron neutron capture therapy (BNCT), a tumor cell-targeted radiotherapy that has demonstrated significant superiority over conventional radiotherapies. Unfortunately, BNCT requires an atomic reactor which is not readily available at hospitals.

Glioblastoma Multiforme is the most common and the most malignant glia tumors in brain cancer. The tumor is composed heterogeneous population cancer cells that make the healing progress after the treatment poor. Although the development of nanoscale systems has successfully improved the way of drug and gene therapy, brain is a complicated multi-cell organ that it is important to have safe and efficacy treatments between cancer tissues and healthy brain cells.

SUMMARY OF THE INVENTION

Accordingly, one scope of the invention is to provide a novel therapy method by utilizing radiation enhancer-incorporated nanocarriers and 5-aminolevulinic acid (5-ALA) sonic-sensitizer, which is able to combine sonodynamic therapy with low dose radiation therapy to protect healthy cells and cancer cells effectively. Moreover, according to the therapy method of the invention, the GBM/Astrocyte kill ratio elevates several times compares to control group.

A method, according to a preferred embodiment of the invention, for treating a patient being afflicted with GBM, firstly, is to administer a plurality of radiation enhancer-incorporated nanocarriers to a treatment site of the patient. Next, the method of the invention is to administer a 5-aminolevulinic acid (5-ALA) to the treatment site of the patient, where the 5-ALA is transformed to protoporphyrin IX (PpIX) in GBM tumor cells the treatment site of the patient. Subsequently, the method of the invention is to apply an ultrasound to the treatment site of the patient. Finally, the method of the invention is to apply a radiation to the treatment site of the patient.

In one embodiment, the each radiation enhancer-incorporated nanocarrier can be an Au-core/$SiO_2$-shell nanoparticle wrapped by a plurality of hyaluronic acid molecules.

In one embodiment, the radiation enhancer-incorporated nanocarriers have a mean particle size in a range of from 26 nm to 450 nm, and the radiation enhancer-incorporated nanocarriers have a concentration in a range of from 10 μg/ml to 3 g/ml.

In one embodiment, the hyaluronic acid molecules have a molecular weight in a range of from 3,000 Daltons to 3,000,000 Daltons.

In one embodiment, the ultrasound has a frequency in a range of from 1 MHz to 8 MHz. In one embodiment, the ultrasound has a preferred frequency in a range of from 1 MHz to 3 MHz.

In one embodiment, the step of applying the ultrasound takes from 1 minute to 24 hours.

In one embodiment, the step of applying the radiation takes from 30 minutes to 4 hours.

In one embodiment, the radiation is an x-ray or a γ-ray.

In one embodiment, the radiation is an x-ray, and the step of applying the radiation has a single dose of from 1 Gy to 10 Gy.

In one embodiment, the radiation is an x-ray, and the step of applying the radiation has a preferred single dose of from 2 Gy to 4 Gy.

Distinguishable from the prior arts, the method of the invention is a non-invasive treatment that requires only low-dosage radiotherapy, and is more effective at killing GBM tumor cells. Moreover, the method of the invention is able to reduce the chance of recurrence and protect the surrounding healthy tissue to reduce side effects significantly.

The advantage and spirit of the invention may be understood by the following recitations together with the appended drawings.

BRIEF DESCRIPTION OF THE APPENDED DRAWINGS

The patent or application file contains at least one drawing executed in color. Copies of this patent or patent application publication with color drawing(s) will be provided by the Office upon request and payment of the necessary fee.

FIGS. 6A to 6E respectively show cytotoxicity of 100 μg/ml HAc-Au@SiO$_2$ nanocarriers in Astrocyte cells, GBM cells and GSC cells combined with 5-ALA and ultrasound/x-ray therapy.

Figure 7:
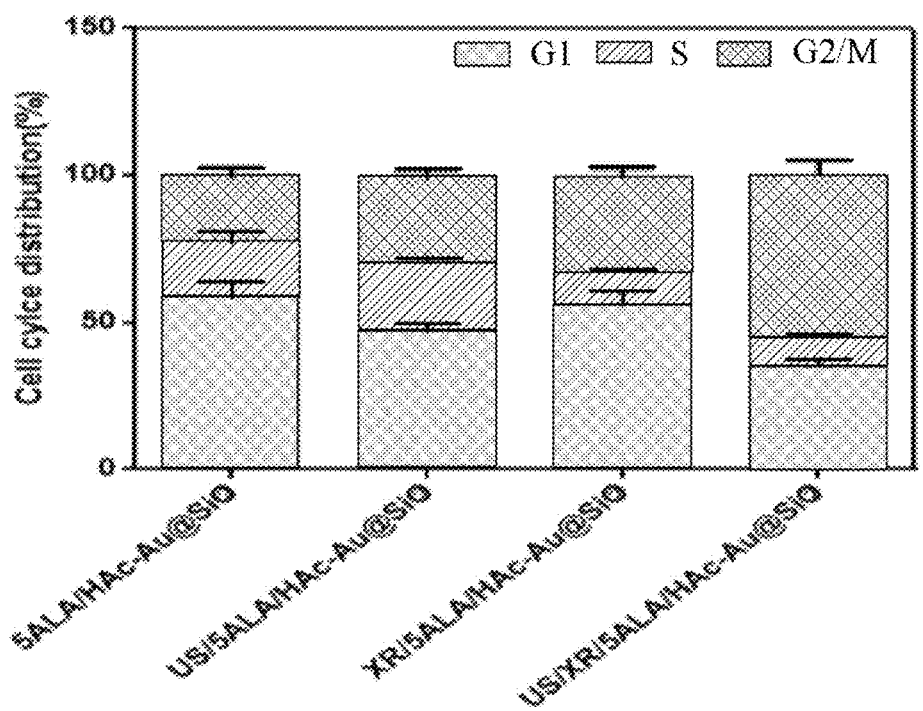

FIG. 7 shows cell cycle distributions of HAc-Au@SiO$_2$/5ALA-treated GBM cells in x-ray irradiation/ultrasound bombardment-induced G2/M phase.

Figure 8:
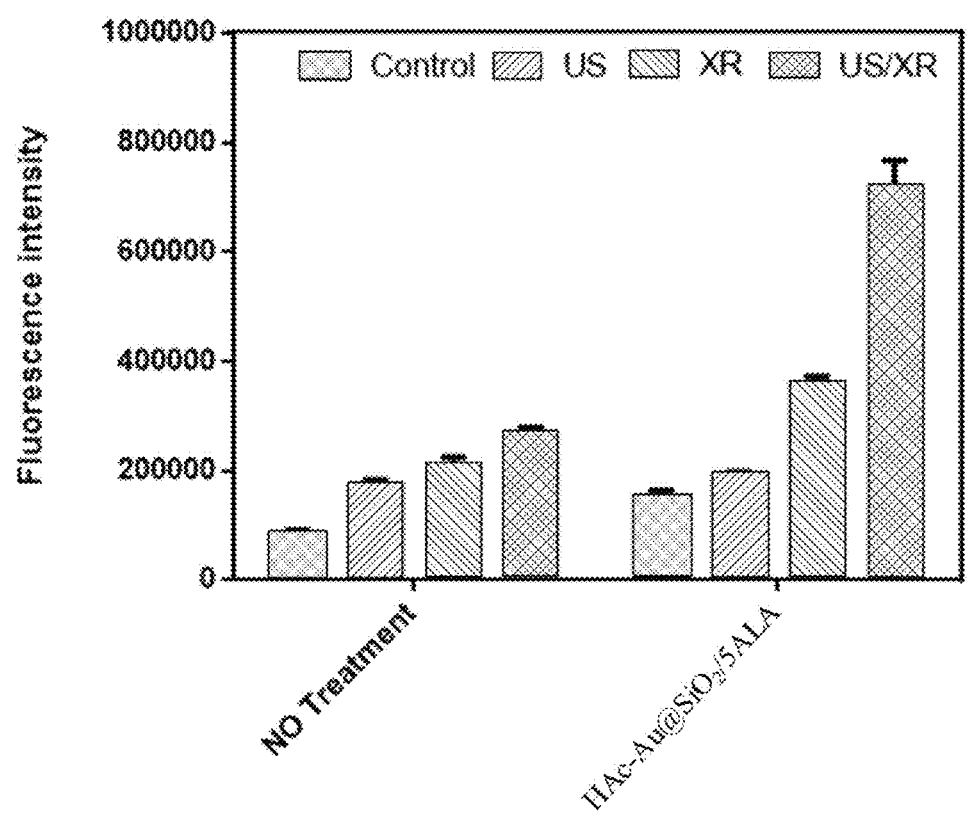

FIG. 8 shows intracellular production of reactive oxygen species (ROS) in GBM cells using flow cytometric analyses.

Figure 9:
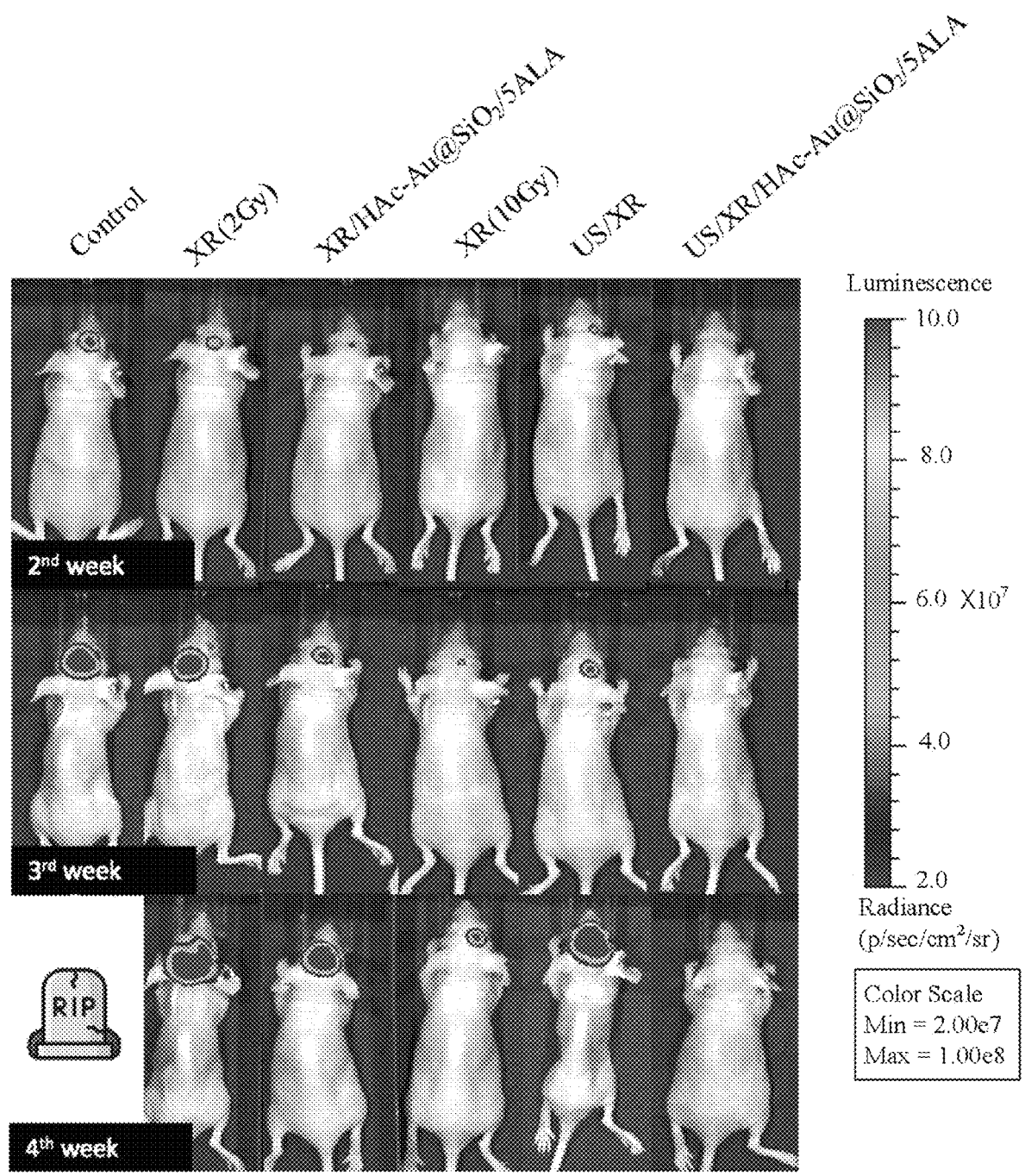

FIG. 9 shows stereotactic intracranial implantation and in vivo bioluminescent imaging of tumor xenografts in a tumor recurrence model of glioblastoma multiforme.

DETAILED DESCRIPTION OF THE INVENTION

A method, according to a preferred embodiment of the invention, for treating a patient being afflicted with GBM, firstly, is to administer a plurality of radiation enhancer-incorporated nanocarriers to a treatment site of the patient. In practical application, the treatment site of the patient is an intracranial space after GBM cutting out surgery.

Next, the method of the invention is to administer a 5-aminolevulinic acid (5-ALA) to the treatment site of the patient, where the 5-ALA is transformed to protoporphyrin IX (PpIX) in GBM tumor cells the treatment site of the patient.

Subsequently, the method of the invention is to apply an ultrasound to the treatment site of the patient.

Finally, the method of the invention is to apply a radiation to the treatment site of the patient.

In one embodiment, the each radiation enhancer-incorporated nanocarrier can be an Au-core/SiO$_2$-shell nanoparticle wrapped by a plurality of hyaluronic acid molecules (HAc-Au@SiO$_2$).

Regarding preparation of HAc-Au@SiO2 nanocarriers, firstly, by a synthesis process, thermally stable gold-mesoporous SiO$_2$ (Au@ mesoporous SiO$_2$; core-shell) nanoparticles are obtained. Then, the Au@ mesoporous SiO$_2$ nanoparticles are made have amino (—NH2) surface by use of APTES ((3-Aminopropyl)triethoxysilane). Next, by grafting of EDC (ethyl-3-(3-dimethylaminopropyl)carbodiimide hydrochloride) and NHS (N-Hydroxysuccinimide), hyaluronic acid molecules with carboxyl (—COOH) (hyaluronic acid (Hyaluronic Acid) are via covalent bonds grafted on the periphery of the nanoparticles to form HAc-Au@SiO2 nanocarriers. It is confirmed that the HAc-Au@SiO2 nanocarriers are stable in the solution and have obvious difference of phagocytosis between normal cells and tumor cells.

Figure 1A:
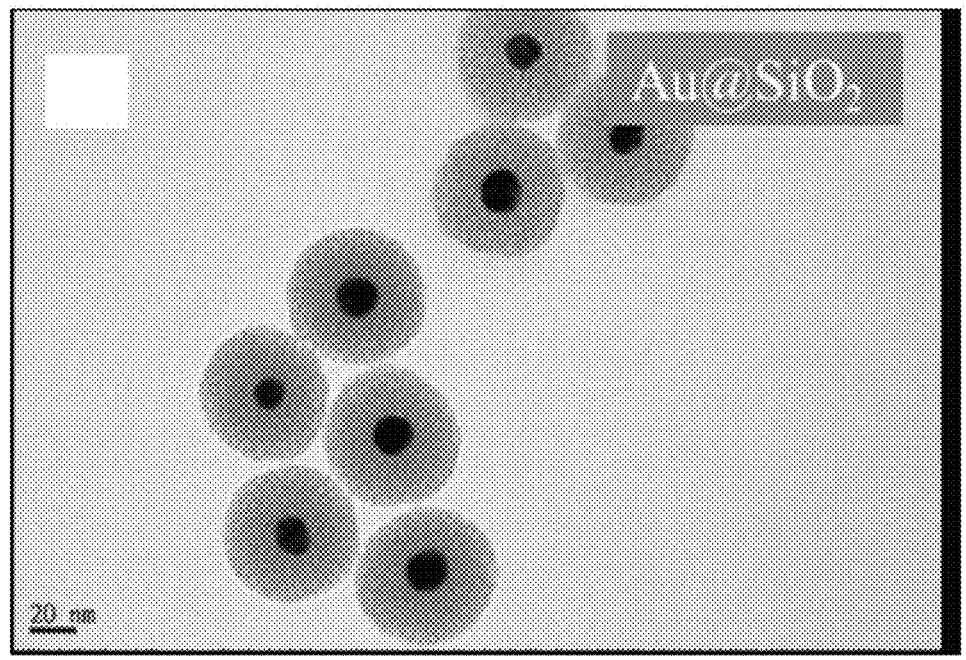
FIG. 1A shows a TEM (transmission electron microscope) photograph of HAc-Au@$SiO_2$ nanocarriers uniformly dispersed in the solution.
Figure 1B:
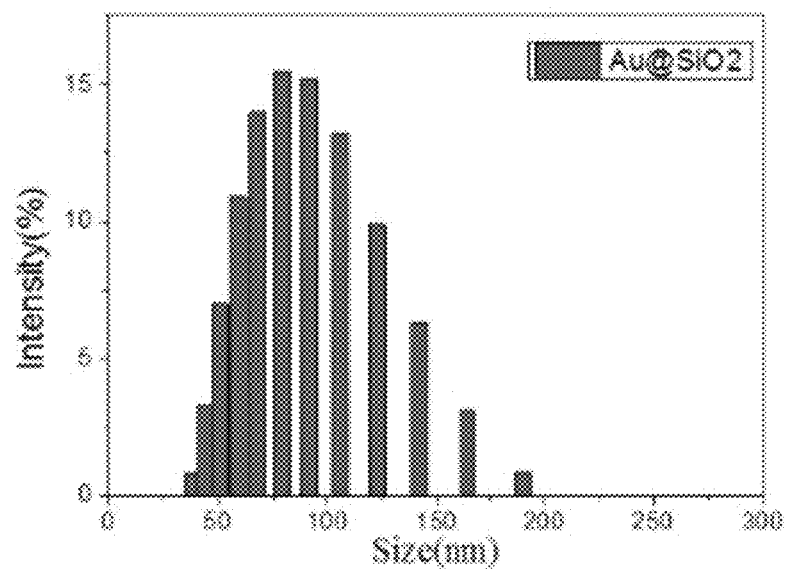
FIG. 1B shows the particle size distribution of the Au@$SiO_2$ nanoparticles.

Referring to FIG. 1A, by using TEM, it is observed that the HAc-Au@SiO$_2$ nanocarriers are uniformly dispersed in the solution and the morphology of the Au@SiO2 nanoparticles exhibit gold nanoparticles wrapped by mesoporous SiO$_2$. The particle size distribution of the Au@SiO$_2$ nanoparticles is shown in FIG. 1B.

Figure 1C:
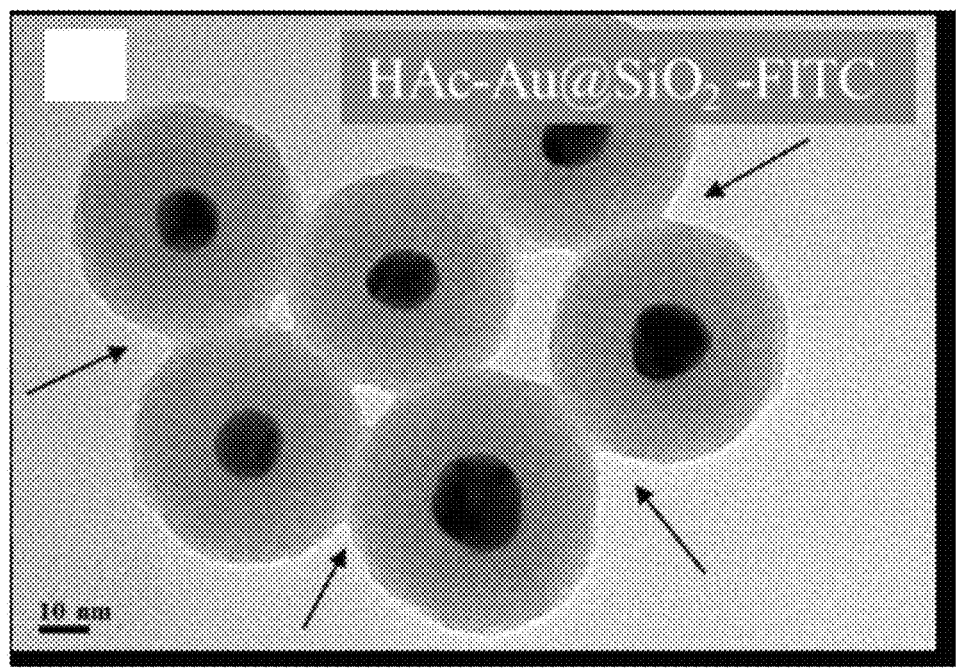
FIG. 1C shows a TEM photograph of HAc-Au@$SiO_2$ nanocarriers wrapped by a thin layer of hyaluronic acid.
Figure 1D:
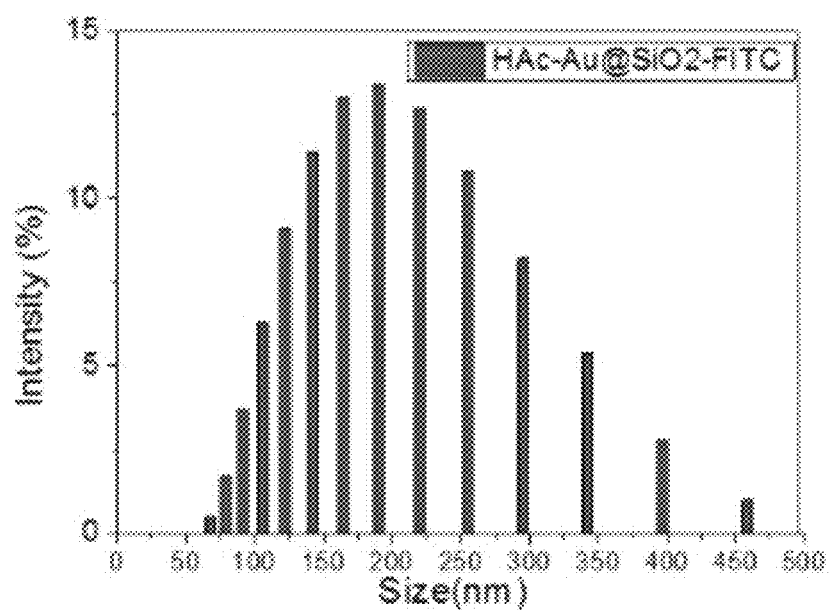
FIG. 1D shows the particle size distribution of the HAc-Au@$SiO_2$-FITC nanocarriers.

Referring to FIG. 1C, by using TEM, it is observed that the HAc-Au@SiO$_2$ nanocarriers are wrapped by a thin layer of hyaluronic acid, and that the holes of mesoporous SiO$_2$ are filled. In FIG. 1C, the notation "HAc-Au@SiO$_2$-FITC" represents HAc-Au@SiO$_2$ nanocarrier grafting with FITC (Fluorescein isothiocyanate). The particle size distribution of the HAc-Au@SiO$_2$-FITC nanocarriers is shown in FIG. 1D.

In one embodiment, the radiation enhancer-incorporated nanocarriers (HAc-Au@SiO$_2$) have a mean particle size in a range of from 26 nm to 450 nm.

Figure 2:
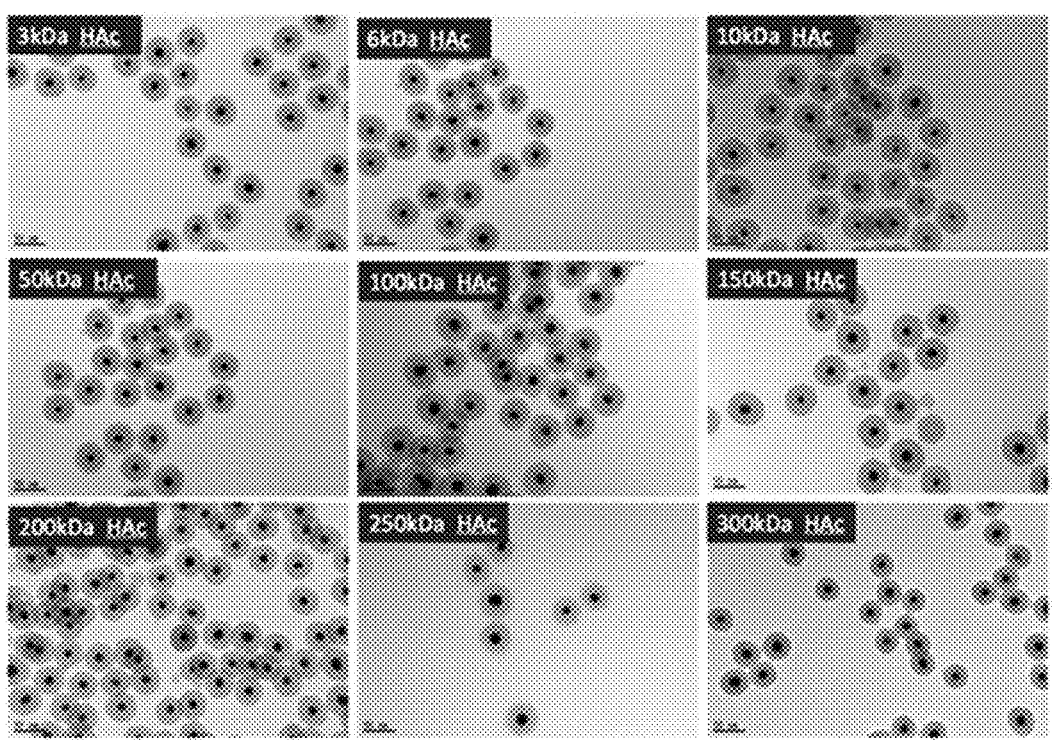
FIG. 2 shows TEM photographs of different molecular weight hyaluronic acid synthesized HAc-Au@$SiO_2$ nanocarriers.

Referring to FIG. 2, by using TEM, photographs of different molecular weight hyaluronic acid synthesized HAc-Au@SiO$_2$ nanocarriers are shown in FIG. 2. In one embodiment, the hyaluronic acid molecules have a molecular weight in a range of from 3,000 Daltons to 3,000,000 Daltons.

Figure 3A:
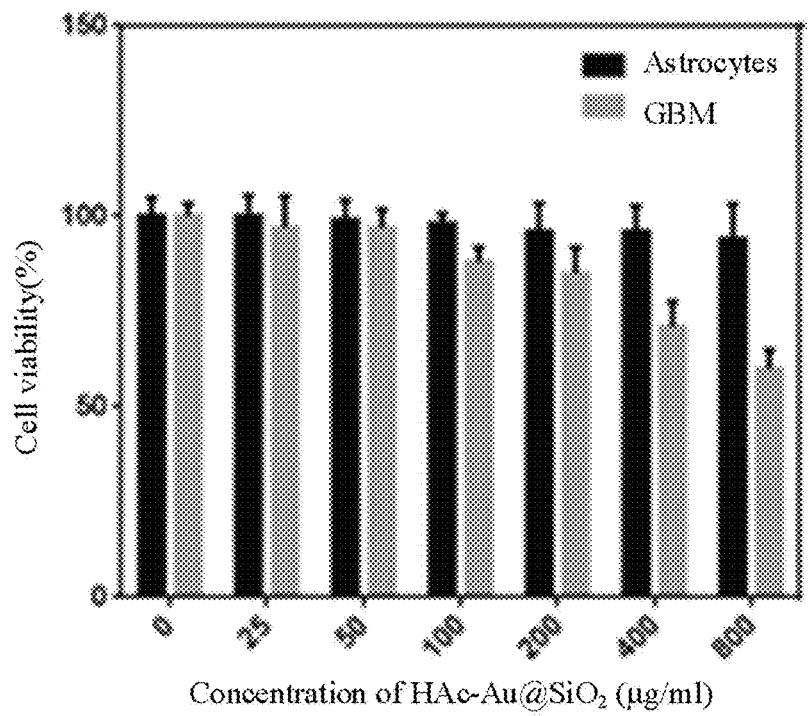
FIG. 3A shows cytotoxicity of Astrocyte and GBM incubated with different concentrations of HAc-Au@SiO2 nanocarriers.
Figure 3B:
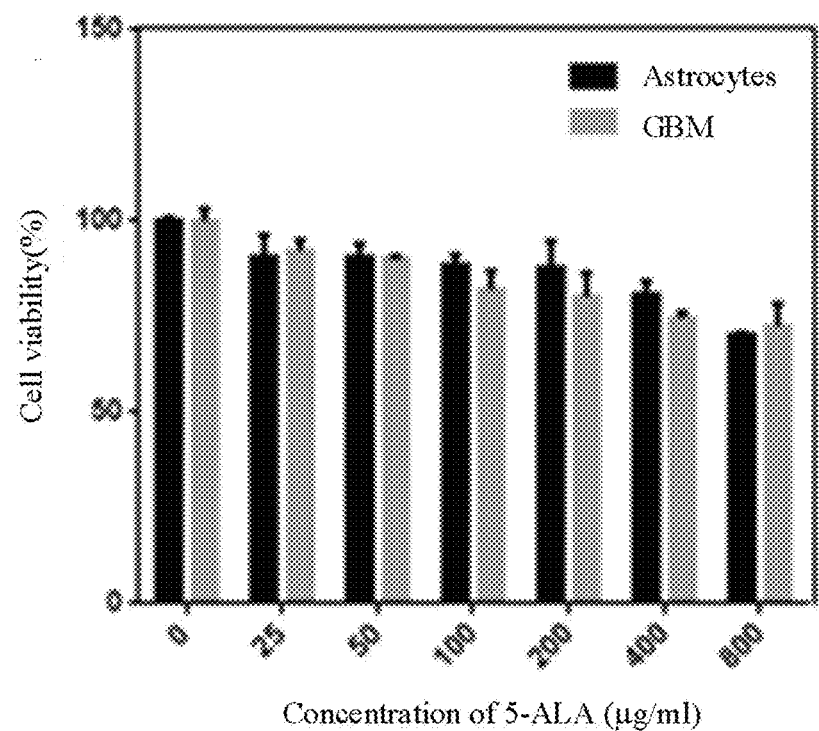
FIG. 3B shows cytotoxicity of Astrocyte and GBM incubated with different concentrations of 5-ALA.

Referring to FIG. 3A and FIG. 3B, the test result of cytotoxicity of Astrocyte (normal cells) and GBM (cancer cell), which are incubated with different concentrations of HAc-Au@SiO2 nanocarriers for 24 hours at 37° C., is shown in FIG. 3A. The test result of cytotoxicity of Astrocyte (normal cells) and GBM (cancer cell), which are incubated with different concentrations of 5-ALA for 24 hours at 37° C., is shown in FIG. 3B.

In one embodiment, the radiation enhancer-incorporated nanocarriers (HAc-Au@SiO$_2$) used in the invention have a concentration in a range of from 10 μg/ml to 3 g/ml.

5-ALA, a FDA-approved drug, will be specifically transformed to protoporphyrin IX (PpIX) in GBM tumor cells. It is well-known that PpIX is a photo/sono-sensitizer which can be activated by visible light (i.e., photodynamic therapy). However, the penetration depth of visible light into tissues is shallow. It is confirmed that PpIX can also be activated by ultrasound sonication (i.e., sonodynamic therapy). The penetration depth of ultrasound into tissues is deep. In this present invention, 5-ALA can be administered via oral route or intravenous route.

It is observed that PpIX is mainly accumulated in the inner mitochondrial. With fluorescence staining, mitochondria co-localization of PpIX in GBM cells (in vitro) can be found. Subsequently, a large number of singlet oxygens and reactive oxygen species (ROS) can be produced by treatment to result in loss of membrane potential and damage of ATP (adenosine triphosphate) produced by mitochondria, and then the damage of GBM tumor cells will lead to the fate of cell apoptosis.

It is also confirmed that the HAc-Au@SiO$_2$ nanocarriers and PpIX have co-localization in GBM tumor cells (in vitro). That means that the HAc-Au@SiO$_2$ nanocarriers will enter into the mitochondria. Once the HAc-Au@SiO$_2$ nanocarriers is co-localized with PpIX, further treatment can enhance the effect and achieve the best therapeutic effect to achieve the best effect. The route of killing is also by producing lots of ROS from the mitochondria to damage the tumor cells.

Figure 4:
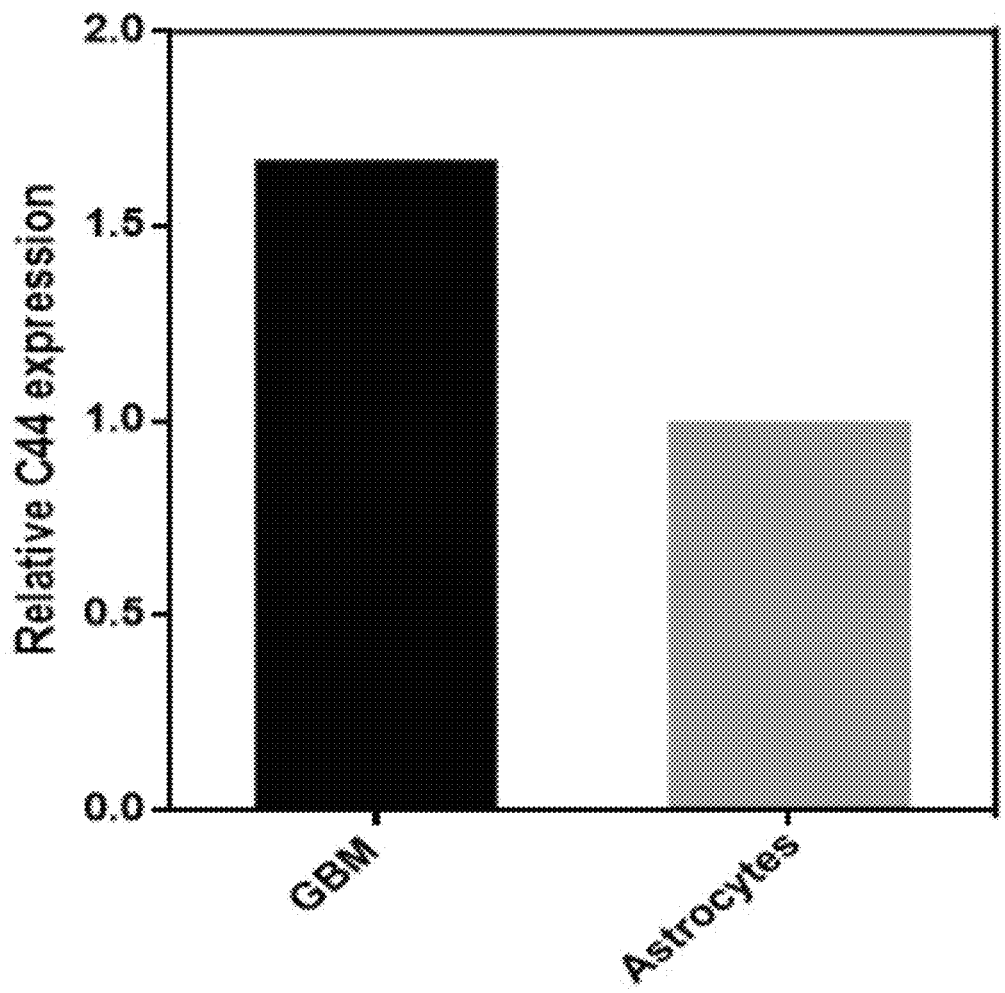
FIG. 4 shows comparison result of cellular uptake of HAc-Au@$SiO_2$ nanocarriers into GBM and Astrocyte cells.

Referring to FIG. 4, by CD44 protein expression analysis in GBM and Astrocyte cells microenvironment, the comparison result of cellular uptake of HAc-Au@SiO$_2$ nanocarriers into GBM and Astrocyte cells is shown in FIG. 4. The result shows that there are more nanocarriers accumulation in GBM cells. Although there also are nanocarriers phagocytosed by astrocyte cells, the accumulation amount of nanocarriers in astrocyte cells is far below the accumulation amount of nanocarriers in tumor cells. Therefore, the HAc-Au@SiO2 nanocarriers can accumulate effectively in tumor cells, and there are selective phagocytosis differences between tumor tissues and normal cells, so that subsequent treatment can protect normal cells and selectively kill tumor cells.

In one embodiment, the radiation is an x-ray or a γ-ray.

Hereinafter, x-ray is taken as an example to illustrate this present invention. While the PpIX transformed from 5-ALA and the radiation enhancer-incorporated nanocarriers delivered into intracranial space (treatment site) are accumulated in GBM tumor cells and/or GBM stem cells, ultrasound is applied to activate the PpIX molecules located in the cerebrospinal fluid filling in the cutting out region, in the near-surface layer of cutting edge and far away from the cutting edge. Hence, the residual tumor cells and GBM stem cells after removing GBM tumor issue will be killed or weakened by photodynamic therapy and sonodynamic therapy. After that, a low-dose X-ray can be employed to interact with photo/sono-sensitizers and radiation enhancer-incorporated nanocarriers. While X-ray hits radiation enhancer-incorporated nanocarriers, more low-energy photons (few eV) and Auger electrons will be generated to further activate photo/sono-sensitizers and/or directly kill the residual tumor cells and GBM stem cells. Therefore, only proportion of the normal dose can realize tumor cell-targeted radiotherapy.

In one embodiment, the radiation is an x-ray, and the step of applying the radiation has a single dose of from 1 Gy to 10 Gy.

In one embodiment, the radiation is an x-ray, and the step of applying the radiation has a preferred single dose of from 2 Gy to 4 Gy.

In one embodiment, the step of applying the radiation takes from 30 minutes to 4 hours.

Figure 5:
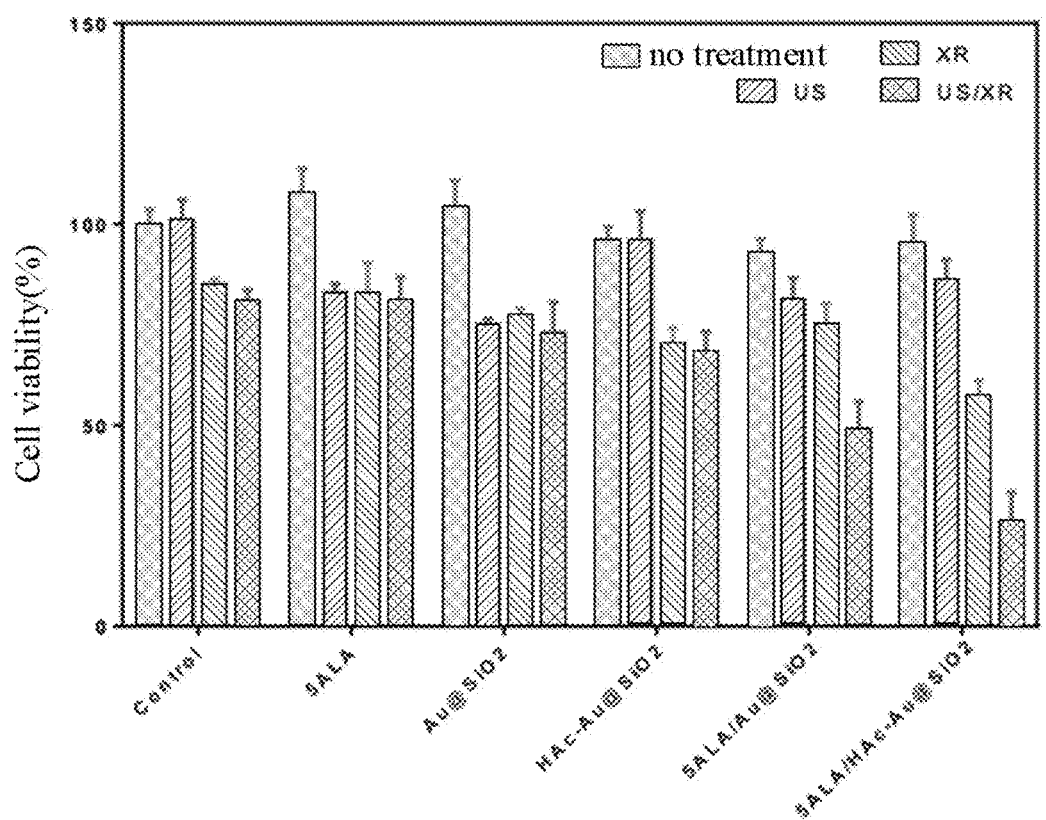
FIG. 5 shows cytotoxicity of 100 μg/ml HAc-Au@$SiO_2$ nanocarriers in GBM cells combined with 5-ALA and US/XR therapy.

Referring to FIG. 5, the result of cytotoxicity of 100 μg/ml HAc-Au@SiO$_2$ nanocarriers in GBM cells combined with 5-ALA and US/XR therapy in 24 hr. is shown in FIG. 5. In vitro efficacy of US/XR therapy is evaluated by collecting PrestoBlue® Cell Viability Reagent data from GBM cells receiving differing samples and dynamic treatments. HAc-Au@SiO$_2$ nanocarrier concentration is 100 μg/ml, Au@SiO$_2$ nanoparticle concentration is 100 μg/ml. Herein, notation "US" represents ultrasound bombardment, 1 MHz, 0.4 W/cm$^2$, and 20% duty ratio for 5 min; notation "XR" represents X-ray irradiation, 6 MV, total dose of 2 Gy in a single fraction; notation "US/XR" represents ultrasound bombardment followed by X-ray irradiation. The result shown in FIG. 5 confirms that the therapy method of the invention by utilizing HAc-Au@SiO$_2$ nanocarriers with 5-ALA photo/sono-sensitizer, which is able to combine sonodynamic therapy with low dose radiation therapy, can kill GBM tumor cells effectively.

Figure 6A:
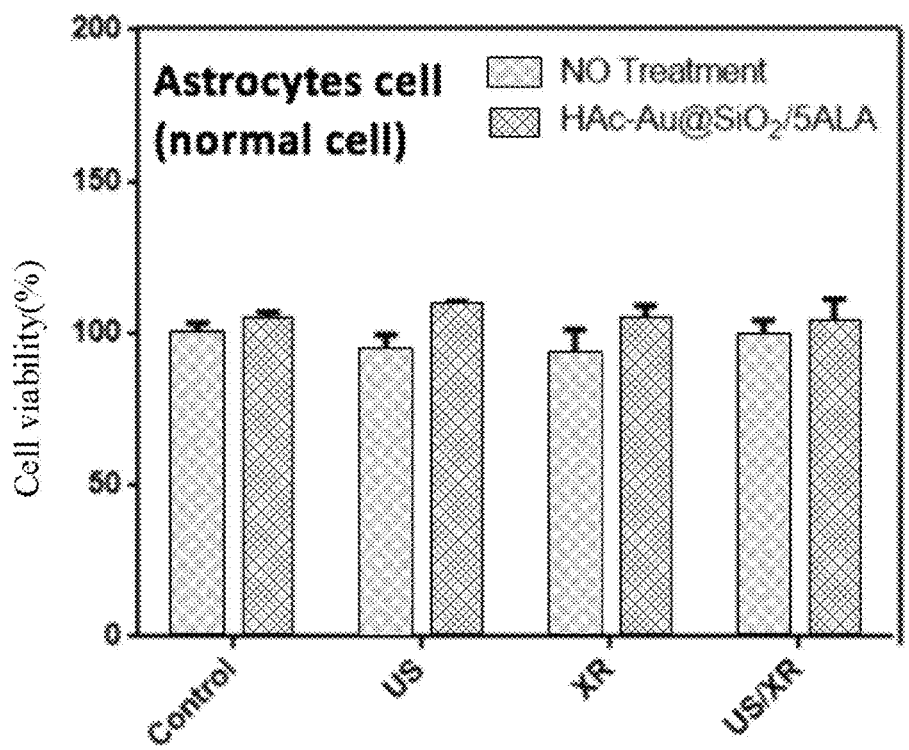
Figure 6B:
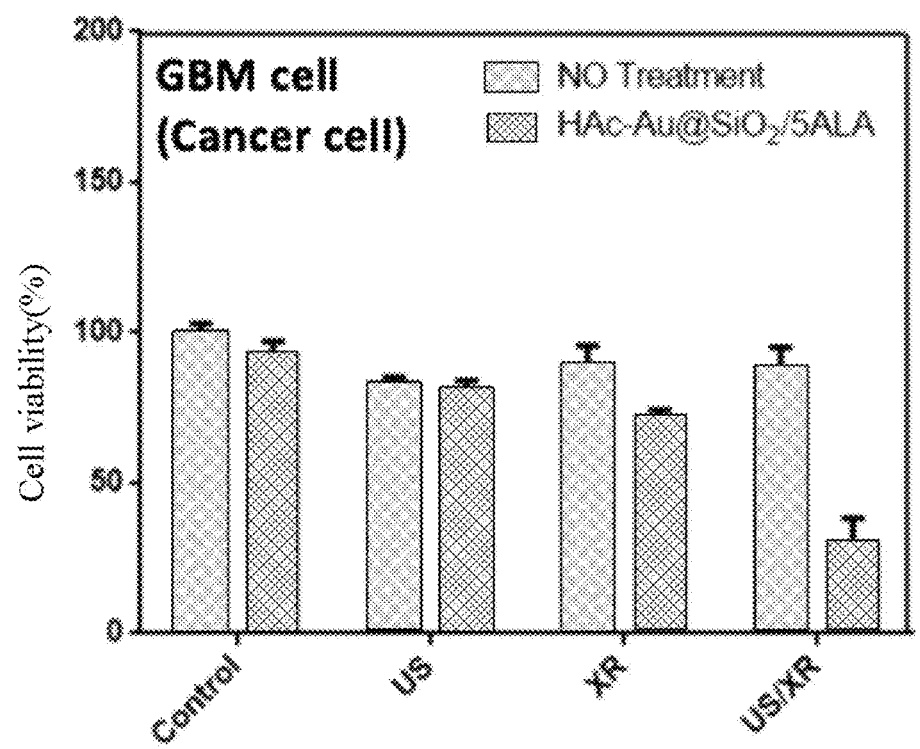
Figure 6C:
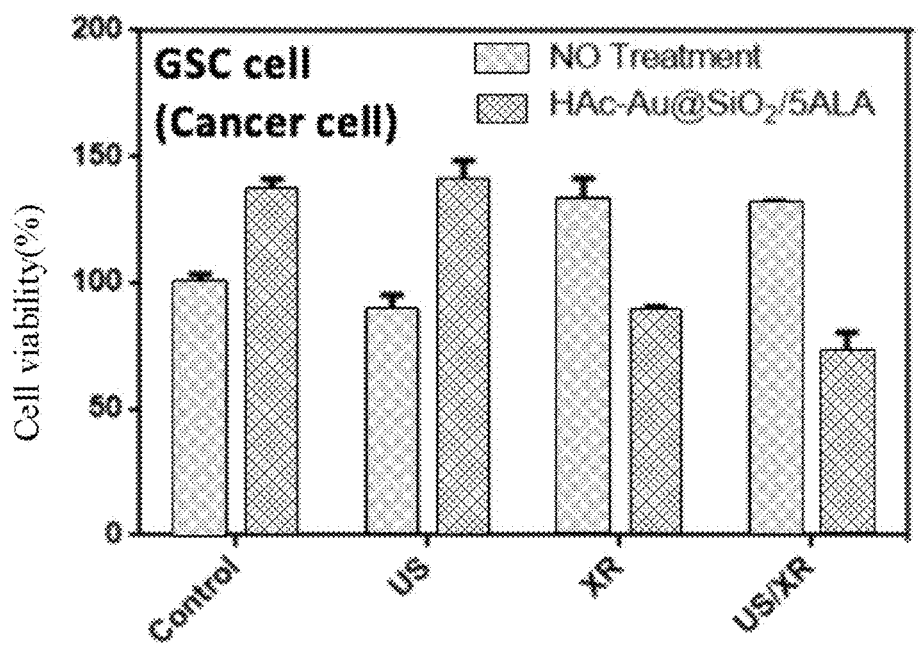
Figure 6D:
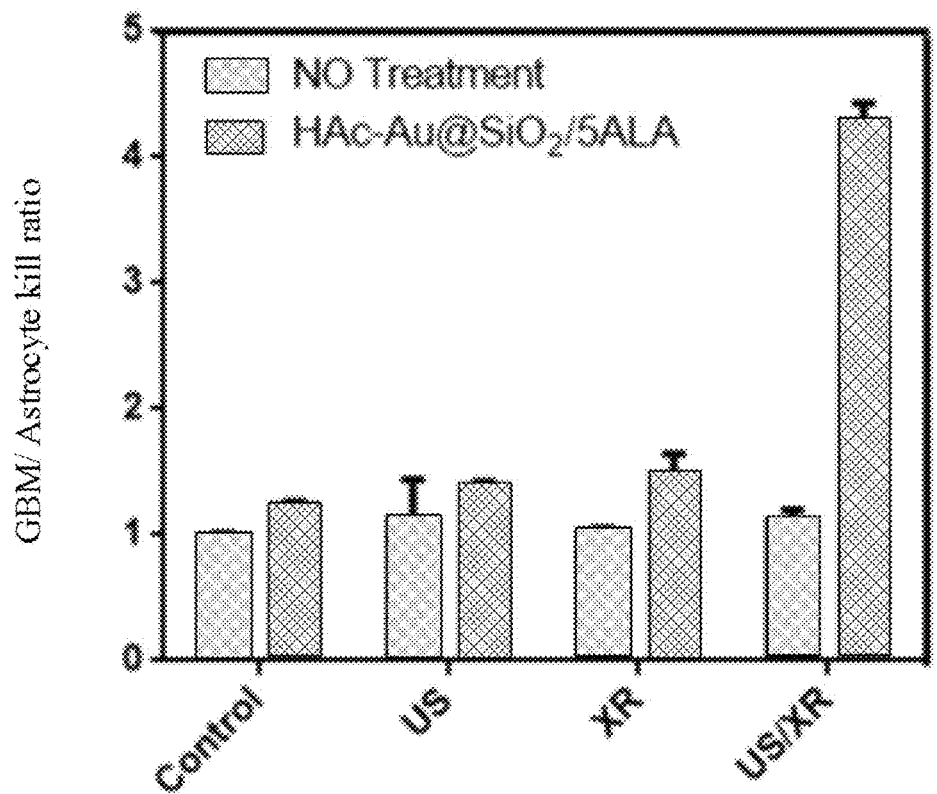
Figure 6E:
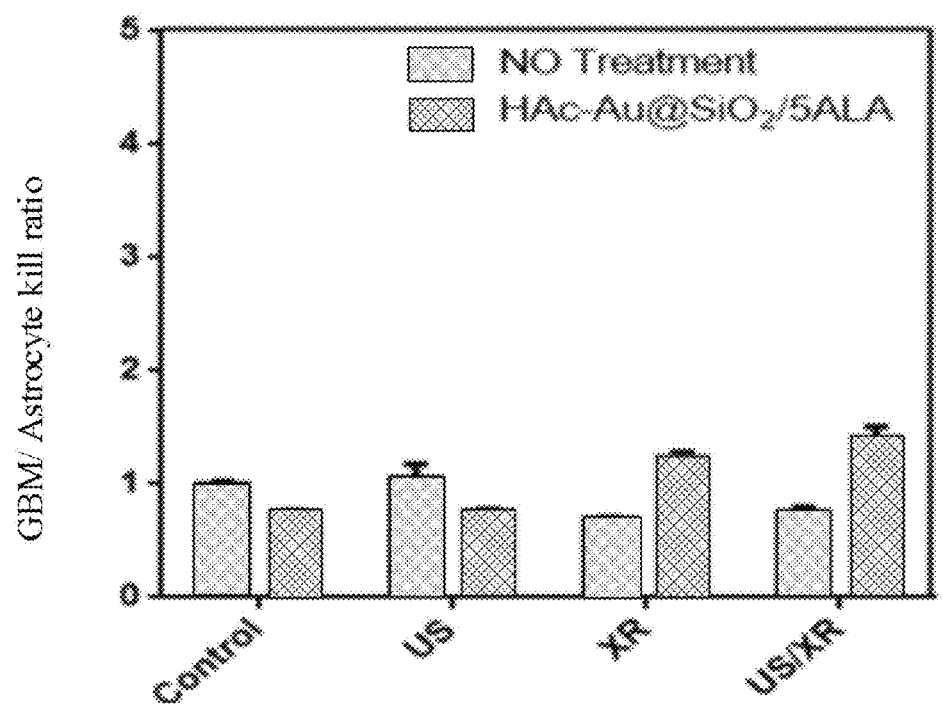

Referring to FIG. 6A to FIG. 6E, the results of cytotoxicity of 100 μg/ml HAc-Au@SiO$_2$ nanocarriers in Astrocyte cells, GBM cells and GSC (glioblastoma stem cell) cells combined with 5-ALA and US/XR therapy in 24 hr. are respectively shown in FIG. 6A, FIG. 6B and FIG. 6C. The GBM cell/Astrocyte cell kill ratio is shown in FIG. 6D. The GSC cell/Astrocyte cell kill ratio is shown in FIG. 6E. In vitro tumor cell-targeted toxicity of US/XR therapy is evaluated by collecting PrestoBlue® Cell Viability Reagent data from Astrocyte normal cells, GBM cancer cells and glioblastoma stem cell receiving US/XR treatment. HAc-Au@SiO$_2$ nanoparticle concentration is 100 μg/ml, Au@SiO$_2$ concentration is 100 μg/ml. The results shown in FIGS. 6A to 6E confirm that the therapy method of the invention by utilizing HAc-Au@SiO$_2$ nanocarriers with 5-ALA photo/sono-sensitizer, which is able to combine sonodynamic therapy with low dose radiation therapy, can kill GBM tumor cells effectively and protect healthy cells.

Referring to FIG. 7, the result of cell cycle distributions of HAc-Au@SiO$_2$/5ALA-treated GBM cells in x-ray irradiation/ultrasound bombardment-induced G2/M phase arrest by flow cytometric analysis is shown in FIG. 7. GBM cells are treated with HAc-Au@SiO$_2$/5ALA receiving sonodynamic therapy and/or radiotherapy, then fixed, stained with PI (propidium iodide), and analyzed by flow cytometry. The results shown in FIG. 7 confirms that the therapy method of the invention promotes cell cycle arrest in G2/M period.

In one embodiment, the ultrasound has a frequency in a range of from 1 MHz to 8 MHz. The ultrasound has a preferred frequency in a range of from 1 MHz to 3 MHz.

In one embodiment, the step of applying the ultrasound takes from 1 minute to 24 hours.

Referring to FIG. 8, the result of intracellular production of reactive oxygen species (ROS) in GBM cells using flow cytometric analyses is shown in FIG. 8. In FIG. 8, schedule of 5-ALA and HAc-Au@SiO$_2$ treatment, exposure of ultrasound bombardment or x-ray irradiation or both, and detection of ROS. Cells is incubated with 200 μg/ml 5-ALA and 100 μg/ml HAc-Au@SiO$_2$ for 6 hr. Detection of ROS is by an oxidant-sensitive fluorescent probe (DCFD). Control is the intracellular ROS levels in cells without ultrasound bombardment or exposure to ionizing irradiation. Other conditions include HAc-Au@SiO$_2$ concentration: 100 μg/ml, US: ultrasound bombardment, 1 MHz, 0.4 W/cm$^2$, and 20% duty ratio for 5 min; XR: X-ray irradiation, 6 MV, total dose of 2 Gy in a single fraction; US/XR: ultrasound bombardment followed by X-ray irradiation. The result shown in FIG. 8 confirms that by the therapy method of the invention, GBM cells produce numbers of reactive oxygen species (ROS) that lead to a decline of mitochondrial membrane potential (MMP). Therefore, cells are fail to generate ATP which can activate the p53 pathway to promote the release of Cytochrome C and then activate Caspase-3. Activation of Caspase-3 not only causes cell damage and may lead to cell apoptosis, but also promote cell cycle arrest in G2/M period.

Referring to FIG. 9, stereotactic intracranial implantation and in vivo bioluminescent imaging of tumor xenografts in a tumor recurrence model of glioblastoma multiforme is shown in FIG. 9. In FIG. 9, the tumor recurrence model is designed as follows the cells were planted in the brains of mice after the treatment process is designed, and the tumor growth is monitored for continuous time to further evaluate the tumor recurrence. Other conditions include HAc-Au@SiO$_2$ concentration: 100 μg/ml, US: ultrasound bombardment, 1 MHz, 1 W/cm$^2$, and 20% duty ratio for 5 min; XR: X-ray irradiation, 6 MV, total dose of 2 Gy in a single fraction; US/XR: ultrasound bombardment followed by X-ray irradiation; cell: GL261; mouse: nude mice. FIG. 9 shows that in the animal experiment, combined with nanocarrier, 5-ALA and treatment can effectively reduce tumor growth. The therapy method of the invention is a non-invasive treatment that require only low-dosage radiotherapy, and is more effective at killing cancer cells. In addition, this novel treatment is able to reduce the chance of recurrence and protect the surrounding healthy tissue to reduce side effects significantly.

To sum up, the description of the above-mentioned preferred embodiments is for providing a better understanding on the strengths and spirits of this present invention, not for limiting the domain of the invention. Moreover, it aims to include various modification and arrangement parallel in form into the domain of the patent applied by this present invention. Due to the above mentioned, the domain of the patent applied by the invention should be explained in a macro view to cover all kinds of possible modification and arrangement of equal form.

What is claimed is:

1. A method for treating a patient being afflicted with glioblastoma multiforme (GBM), said method comprising the steps of:

administering a plurality of radiation enhancer-incorporated nanocarriers to a treatment site of the patient, wherein each radiation enhancer-incorporated nanocarrier is an Au-core/SiO$_2$-shell nanoparticle wrapped by a plurality of hyaluronic acid molecules, and the radiation enhancer-incorporated nanocarriers have a concentration of 100 μg/ml;

administering a 5-aminolevulinic acid (5-ALA) to the treatment site of the patient, wherein the 5-ALA is transformed to protoporphyrin IX (PpIX) in GBM tumor cells at the treatment site of the patient;

applying an ultrasound having a frequency of 1 MHz to the treatment site of the patient; and applying a radiation having a single dose of 2 Gy to the treatment site of the patient, wherein after implementation of said method, a cell viability of the GBM tumor cells is less than 50%, and a GBM cell/Astrocyte cell kill ratio of the patient is larger than 4.

2. The method of claim 1, wherein the radiation enhancer-incorporated nanocarriers have a mean particle size in a range of from 26 nm to 450 nm.

3. The method of claim 1, wherein the hyaluronic acid molecules have a molecular weight in a range of from 3,000 Daltons to 3,000,000 Daltons.

4. The method of claim 1, wherein the step of applying the ultrasound takes from 1 minute to 24 hours, and the step of applying the radiation takes from 30 minutes to 4 hours.

5. The method of claim 1, wherein the radiation is an x-ray or a γ-ray.

* * * * *